United States Patent
Brady et al.

(10) Patent No.: US 8,522,615 B1
(45) Date of Patent: Sep. 3, 2013

(54) SIMPLIFIED DIRECT-READING POROSITY MEASUREMENT APPARATUS AND METHOD

(75) Inventors: Steven K. Brady, Renton, WA (US); William P. Motzer, Seattle, WA (US); Jeffrey R. Kollgaard, Seattle, WA (US); Nathan R. Smith, Newcastle, WA (US); Nancy Wood, Clayton, MO (US); David Fortner, Sullivan, MO (US)

(73) Assignee: The Boeing Company, Chicago, IL (US)

( * ) Notice: Subject to any disclaimer, the term of this patent is extended or adjusted under 35 U.S.C. 154(b) by 230 days.

(21) Appl. No.: 12/956,436

(22) Filed: Nov. 30, 2010

(51) Int. Cl.
   *G01N 29/036* (2006.01)

(52) U.S. Cl.
   USPC ............................................. 73/579

(58) Field of Classification Search
   USPC .............. 73/579, 1.82, 38, 152.05, 588, 609, 73/599, 602
   See application file for complete search history.

(56) References Cited

U.S. PATENT DOCUMENTS

| | | | |
|---|---|---|---|
| 4,184,373 A * | 1/1980 | Evans et al. | 73/588 |
| 7,222,514 B2 | 5/2007 | Kollgaard et al. | |
| 7,337,673 B2 * | 3/2008 | Kennedy et al. | 73/633 |
| 7,562,576 B2 | 7/2009 | Fetzer et al. | |
| 7,574,915 B2 | 8/2009 | Kollgaard et al. | |
| 7,628,075 B2 * | 12/2009 | Kennedy et al. | 73/628 |
| 7,640,810 B2 * | 1/2010 | Kennedy et al. | 73/634 |
| 7,640,811 B2 * | 1/2010 | Kennedy et al. | 73/634 |
| 7,895,895 B2 | 3/2011 | Kollgaard et al. | |
| 2005/0279171 A1 | 12/2005 | Kollgaard et al. | |

* cited by examiner

*Primary Examiner* — Jacques M Saint Surin
(74) *Attorney, Agent, or Firm* — Yee & Associates, P.C.

(57) ABSTRACT

An apparatus for measuring porosity of a structure includes an ultrasonic transducer device configured to be pressed against a structure, the ultrasonic transducer device being further configured to emit ultrasonic pulses into the structure and detect echo profiles; and an electronic device including: a manager having an interface gate, a back-surface sensing gate and a back surface analysis gate; a pulse generator interfacing with the manager and the ultrasonic transducer device; a data acquisition device interfacing with the ultrasonic transducer device and the manager; and a display having a porosity indicator interfacing with the manager.

20 Claims, 7 Drawing Sheets

SIMPLIFIED DIRECT-READING POROSITY MEASUREMENT APPARATUS AND METHOD

TECHNICAL FIELD

Embodiments of the present disclosure relate generally to ultrasonic inspections of structures. More particularly, embodiments of the disclosure relate to apparatuses and methods for the direct numerical reading of the porosity of structures.

BACKGROUND OF THE DISCLOSURE

Laminate composite materials are becoming increasingly common in the construction of large aircraft. Typical laminate composite materials are composed of layered resin-bonded graphite textiles. Assessments of laminate composite materials represent significant challenges with regard to efficiencies in time, cost, and training Factory workers and ground maintenance crews often must use highly sophisticated techniques to make assessments of defective areas.

In manufacture or repair of laminate composite materials, it is often necessary to measure the porosity of the materials to determine if the structure meets engineering requirements. Porosity, quantified by void area over total unit area in a cross section, is recorded as a percentage value. Currently there are no ultrasonic instruments that display this value directly, it must always be estimated by indirect means. Porosity levels are estimated by observing the attenuation of ultrasound energy passing through a composite part. An ultrasonic pulse of varying frequency content, typical of most ultrasound porosity measurement systems, is modified as it passes through porous material. Higher levels of porosity lead to more attenuation of ultrasound energy than do low levels of porosity in a composite part. Low ultrasound frequencies penetrate composite materials better than high ultrasound frequencies. Therefore, at a given porosity level, high frequency ultrasound energy is attenuated comparatively more than low frequency ultrasound energy. The main cause of measurement variability in porosity is the varying high and low frequency content or bandwidth of different sensors and electronic receivers used across the industry. FFT (Fast Fourier Transform) measurements show that the center frequency of an exiting ultrasonic signal is much lower than the center frequency of the entering ultrasound signal. For example, the ultrasound signal received from a transducer with a 5 MHz center frequency may have a mean frequency of 1 MHz once it has passed through porous laminate structure. This frequency-filtering effect of porosity is well-known.

As a result of this frequency-filtering effect, the signal amplitude displayed by a receive transducer in a two-transducer through-transmission configuration is a function of both the frequency content or bandwidth of the receive transducer and the excitation energy and bandwidth of the transmit pulse. The highest excitation energy is centered around the $F_0$ center transmit frequency, but the highest energy in the received signal is dependent upon the wavelength of the sound interacting with the material. Thus, the final result is a combination of two determining factors: the impinging energy (highest at the center frequency of the transmitter) and the transmitted energy (biased toward the lower frequencies in the bandwidth) Therefore, the different frequency content or bandwidth of sensors and receivers used in obtaining porosity measurements is a source of measurement variation, causing them to register different amplitudes for the same porosity content. Reliable measurement requires the use of physical known-porosity standards for calibration of specific equipment, and subsequent control of that equipment since the attenuation curves generated are only valid for that instrument and sensor. In some applications, it may be required that these physical porosity standards be transported to the measurement site and that new porosity standards be produced as needed. However, the cost of producing and transporting porosity standards for porosity measurement purposes may be excessive.

Thus, it would be advantageous to provide apparatuses and methods for inspecting the porosity of structures by eliminating the variation caused by the bandwidth of the interrogating system and receiving systems and displaying the attenuation result as a direct porosity read-out. Once calibrated for a particular laminate material, only a pristine standard (or assumed zero percent porosity area) would be required to conduct examinations in multiple factory locations. Expensive known-porosity standards made of the material would not be necessary.

SUMMARY

The disclosure is generally directed to a diagnostic apparatus for measuring porosity of a structure. An illustrative embodiment of the apparatus includes an ultrasonic transducer device configured to be pressed against a structure, the structure having a front surface and a back surface, the ultrasonic transducer device being further configured to emit ultrasonic pulses into the structure through the front surface and detect echo profiles; and an electronic device including: a manager having an interface gate adapted to cover a front surface ultrasonic pulse entering the front surface of the structure, a back-surface sensing gate adapted to cover an interval from beyond the front surface of the structure to an end point far out in time and a back surface analysis gate adapted to center over the back surface of the structure and define limits of a signal capture; a pulse generator interfacing with the manager and the ultrasonic transducer device; a data acquisition device interfacing with the ultrasonic transducer device and the manager; and a display having a porosity indicator interfacing with the manager.

The disclosure is further directed to a direct-reading porosity measurement method. An illustrative embodiment of the method includes selecting a structure to be measured, transmitting an ultrasonic signal into the structure, receiving an ultrasonic signal response from the structure, filtering the ultrasonic response, obtaining a reference amplitude for the structure to be measured based on the ultrasonic response, obtaining at least one amplitude variation of the ultrasonic signal response for the structure to be measured, measuring attenuation of the ultrasonic signal by comparing the amplitude variation of the structure to be measured with the reference amplitude; and calculating a porosity level of the structure based on the measured attenuation of the ultrasonic signal.

BRIEF DESCRIPTION OF THE ILLUSTRATIONS

DETAILED DESCRIPTION

The present disclosure now will be described more fully hereinafter with reference to the accompanying drawings, in which some, but not all embodiments of the disclosure are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

Figure 1:
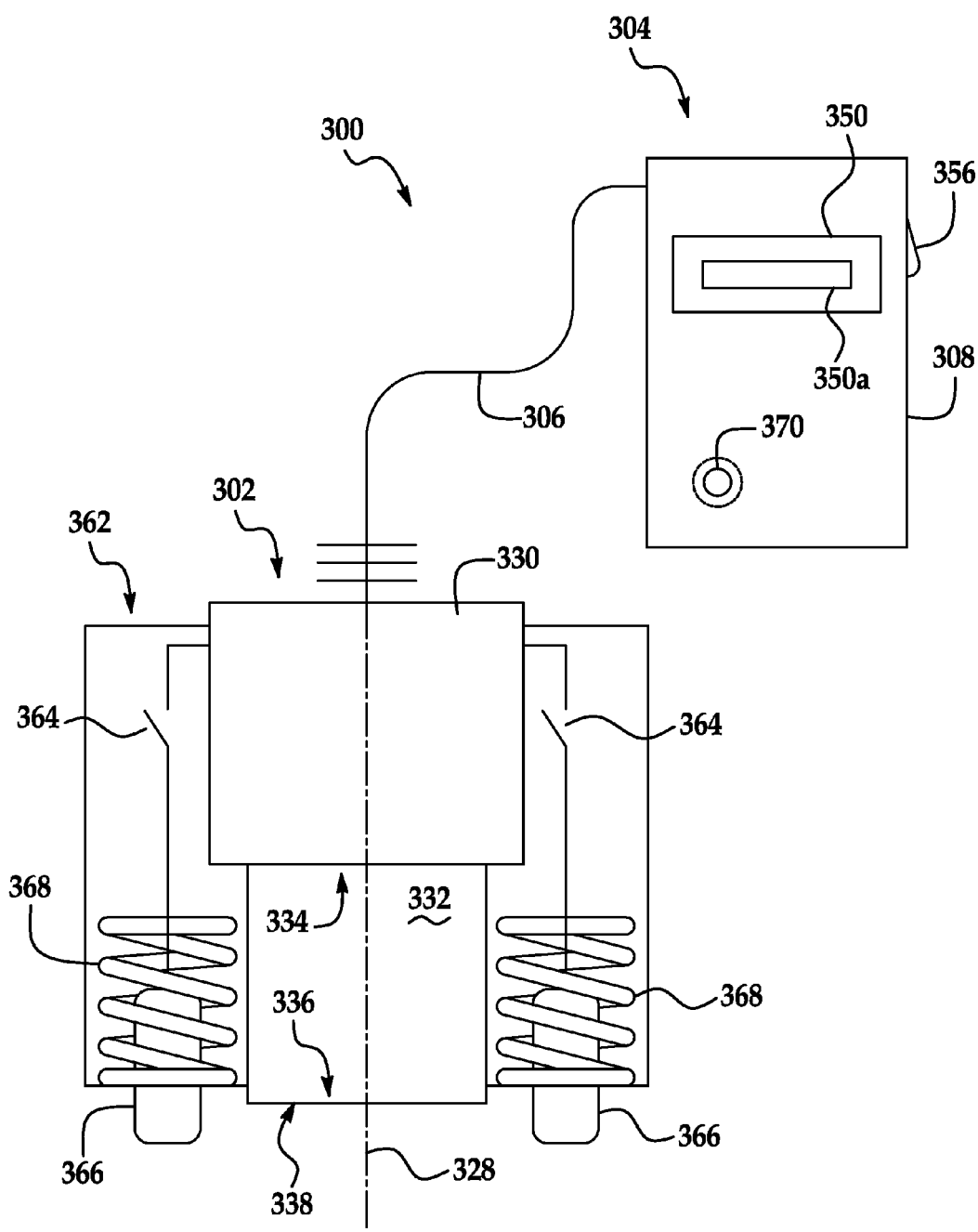
FIG. 1 illustrates a diagnostic apparatus in accordance with one embodiment of the present disclosure, with an ultrasonic transducer device thereof shown in cross-sectional view.

FIG. 1 illustrates a direct-reading porosity measurement apparatus, hereinafter apparatus, according to an embodiment of the present disclosure. The apparatus 300 may include an ultrasonic transducer device 302 and an electronic device 304 having a housing 308, a display 350, a power-switch 356, and a hidden calibration activator 370. The embodiment of the display 350 illustrated in FIG. 1 may include a porosity indicator 350a for indicating the percent porosity of a structure which is measured using the apparatus 300. In some embodiments, the display 350 may include an LCD read-out. The ultrasonic transducer device 302 may include an ultrasonic transducer 330 and a coupling element 332 coupled to the transducer for disposition between the transducer and a surface of a structure under measurement. An activator assembly 362 may be attached to the ultrasonic transducer device 302. As will be described in the following in further detail, when the apparatus 300 is used to measure the porosity of a structure, the ultrasonic transducer device 302 may be pressed against a surface of the structure and the percent porosity of the structure automatically indicated on the porosity indicator 350a. The apparatus 300 may thus be useful to operators who may not be highly trained in sophisticated NDI visualization technologies. For example, a factory worker could use the apparatus 300 to rapidly determine whether attenuative areas identified in normal ultrasonic operations represent porosity levels above or below a certain acceptable threshold.

The ultrasonic transducer 330 may be operable as a pulse-echo inspection sensor that both sends and receives ultrasonic waves. Such transducers are commercially available and can be fabricated, for example, from a polymer-based piezo-electric material called polyvinylidene fluoride (PVDF). The ultrasonic transducer 330 typically sends an ultrasonic pulse into an inspected structure and then generates an electrical signal when an ultrasonic echo signal returns from the structure. Outgoing ultrasonic pulses traveling through a structure tend to reflect from surfaces, edges, and other discontinuities such as damages in the structure. A returning ultrasonic echo signal can include multiple time-distributed return pulses and thus returning ultrasonic echo signals are referred to herein as echo profiles. Typical echo profiles include return pulses reflected from surfaces, adhesive bondlines, and voids. The electrical signal generated by the ultrasonic transducer may convey amplitude and time data corresponding to the amplitudes and arrival times of return pulses within the echo profile. The electronic device 304 may activate the ultrasonic transducer 330 to send outgoing ultrasonic pulses and receive signals generated by the ultrasonic transducer 330 by way of one or more conductive cables 306, which can have a length as desired for holding and moving the ultrasonic transducer device 302 separately from the electronic device 304.

The ultrasonic transducer 330 may define an acoustic axis 328, or maximum response axis, along which outgoing pulses are maximally directed and along which the transducer has maximum sensitivity for detecting returning echo profiles. A coupling element 332 having a proximal end 334 coupled to the transducer 330 and an opposing distal end 336 may be disposed about the acoustic axis 328 for, among other things, coupling the transducer to a structure when the porosity of a structure is to be measured. The distal end 336 may define a generally planar contact surface 338, which may be perpendicular to the acoustic axis 328, for pressing against the surface of a measured structure. The coupling element may be generally constructed of deformable and rubbery acoustic polymer material. The ultrasonic transducer device 302 may be a dedicated device intended toward measuring the porosity of a particular type of structural material. In that context, the coupling element may be acoustic-impedance matched with the particular type of structure material. That is, the coupling element may be constructed of a selected acoustic polymer material having a specific acoustic impedance that approximately matches the specific acoustic impedance of the particular type of structural material. Such impedance matching may promote the transfer of acoustic energy across the junction of the contact surface 338 and the surface of a measured structure, minimizes reflections at the junction, and thus promotes the sensitivity of the ultrasonic transducer 330. Acoustic polymers having various specific acoustic impedance values are known and are commercially available for impedance matching purposes.

Figure 2:
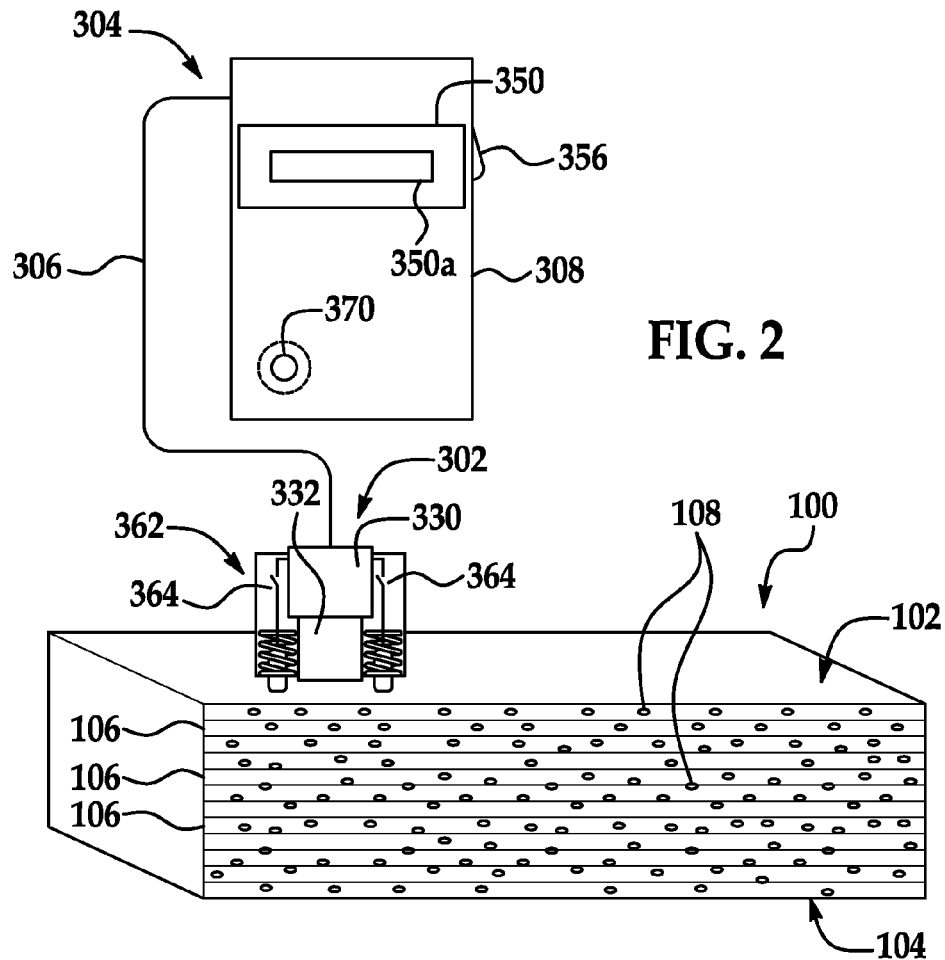
FIG. 2 is a diagrammatic environmental view of the diagnostic apparatus of FIG. 1 shown inspecting a structure having no sub-surface flaws as indicated by a display of the apparatus.

The activator assembly 362 may include multiple switches 364 that permit activation of the ultrasonic transducer 330 when all of the multiple switches are simultaneously actuated. The power switch 356, when opened, may prevent accidental activation of the ultrasonic transducer when the switches are inadvertently pressed such as when the device 302 is carried and stored. Each switch 364 may include a respective contact member 366 biased by a respective spring 368 toward a disposition in which the switch is open. Each switch may close when the respective contact member is pressed against the surface of a structure under measurement. The contact members may be constructed of a material that is durable yet is unlikely to damage a measured structure. For example, the contact members can be constructed of polytetrafluoroethylene (PTFE), which is available from Dupont™ as Teflon®. The multiple switches 364 may together surround the acoustic axis 328 of the ultrasonic transducer 330. The switches may all be simultaneously closed, or actuated, when the ultrasonic transducer device is pressed against a surface such that the contact surface 338 of the coupling element 332 is pressed against, and disposed perpendicular to, the surface of a measured structure. Thus, the activator assembly 362 may provide a convenient triggering advantage, a coupling assurance advantage, and an alignment advantage. The electronic device 304 may be prompted to activate the ultrasonic transducer 330 upon simultaneous actuation of all of the multiple switches, which may require both that the acoustic axis 328 of the transducer 330 is directed perpendicular to the surface of a structure under inspection and that the contact surface 338 of the coupling element firmly contacts the surface of the structure. The diagnostic apparatus 300 is shown in FIG. 2 inspecting a structure 100. The ultrasonic transducer device 302 is shown pressed against a front surface 102 of the structure such that all of the multiple switches of the activator assembly 362 are actuated. The ultrasonic transducer 330 may thus emit one or more ultrasonic pulses into the structure and detect the echo profile 110 shown in FIG. 3.

FIG. 2 depicts an exemplary laminate structure 100 capable of being used on any number of structures, such as those found on airplanes, automobiles and other vehicles, or any other structure that can benefit from a light, yet strong material. The laminate structure 100 may have a front-surface 102 and a back-surface 104 and may include multiple individual laminate sheets 106. The laminate sheets may be joined together by a bonding material. The exemplary laminate sheets 106 may include sheets of graphite fibers joined by a bonding material composed of an ester based resin. However, it should be appreciated that these descriptions may relate to sheets constructed of other materials. Such other materials include, but are not limited to: carbon-based fabrics; metal foils; and polymer-based fabrics such as Kevlar®. Furthermore, while the laminate structure 100 of FIG. 2 is formed using an ester-based resin, these descriptions may relate as well to other bonding materials. In the course of normal use, laminate materials are subject to accidental damages. The laminate structure 100 in FIG. 2 has a concentration of porosity voids 108, which may be associated with a manufacturing flaw or a flaw in a bonded repair.

Figure 3:
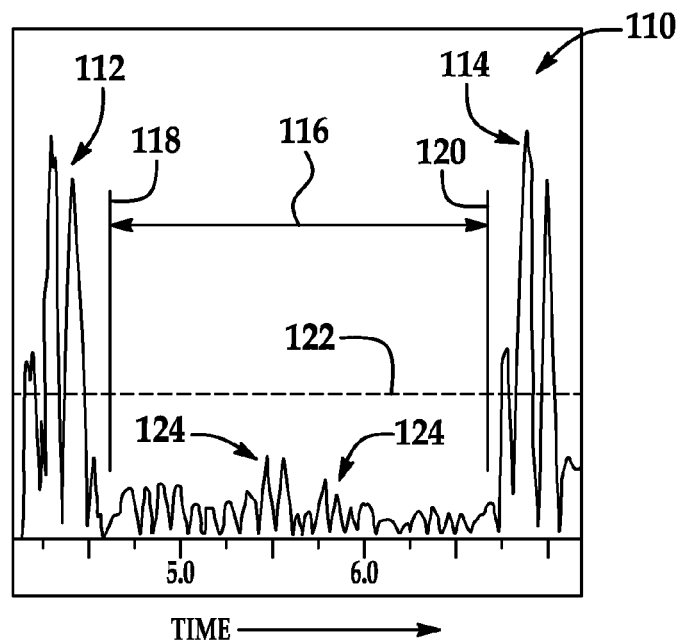
FIG. 3 is a graph of an echo profile generated by the ultrasonic transducer device of FIG. 1 as disposed in FIG. 2.

The electrical waveform 110 shown in FIG. 3 represents the electrical signal generated by the ultrasonic transducer 330 as graphically displayed on an instrument such as an oscilloscope. Electrical fluctuations having various amplitudes rise vertically above the "Time" axis such that early fluctuation events are shown on the left and later subsequent ordered events occurring in time are represented by considering the waveform from left to right. Thus the electrical fluctuation group 112 may be generated by the ultrasonic transducer 330 before the electrical fluctuation group 114. The fluctuation groups 112 and 114 may have respective amplitudes that are greater than those of the minor fluctuations 124. Though the fluctuation groups 112 and 114 may include high-frequency oscillations, such groups will be referred to herein as "echoes." Furthermore, the electrical waveform 110 is appreciated by those skilled in the arts of ultrasonic measurements and NDI technologies as representing multiple time-ordered ultrasonic return echoes from features of an ultrasonically inspected structure. Thus, waveforms such as the electrical waveform 110 will be referred to herein as "echo profiles," and the electrical signals such as the signal 112 and 114 will be referred to herein as "echoes."

The echo profile 110 may include the signal 112 that returned from the front surface 102 of the structure 100 as an echo after an outgoing ultrasonic pulse was sent toward the structure, through the coupling element 332, by the ultrasonic transducer 330. The echo profile also may include the signal 114 that similarly returned as an echo from the back surface 104 of the structure 100. Outgoing pulses are not illustrated as portions of echo profiles herein but should be understood to have occurred at times preceding the front-surface echo in FIG. 3. Some embodiments of the present disclosure may include an acoustic coupling element disposed between an ultrasonic transducer and a front surface of an inspected structure. Such a coupling element may serve to provide dry coupling between the transducer and an interrogated structure and serve as a delay line in that it imposes a delay time, allowing the long-duration initial-pulse signal to be excluded from the display according to the length of the coupling element and according to the speed of ultrasonic pulse transmissions within the coupling element. If an ultrasonic transducer is coupled to a surface without a delay line, the long-duration outgoing pulse, or "main bang" as such pulses are sometimes called, overlaps the echo from the surface. In such a situation, the outgoing pulse and the front-surface echo are difficult, and may be impossible, to separately distinguish and illustrate. However, the coupling element 332 in FIG. 2 may space the ultrasonic transducer 330 from the front surface 102 of the structure under measurement. Thus, the time of flight (TOF) of the front-surface echo 112 may include at least the time required for an outgoing pulse to propagate from the transducer, to the contact face 338 (FIG. 1) of the coupling element, and back to the transducer. Thus, the outgoing pulse would have occurred prior to the time range depicted in FIG. 3. It should be understood that, in this context, the TOF of a return pulse is generally defined as the time elapsed between the time of a transducer's sending of an outgoing pulse and the time of the transducer's receipt of the return pulse. Thus, the "Time" axis of FIG. 3 can be considered a portion of a relative TOF axis, wherein the origin of the axis, as defined by the time of an outgoing pulse, is not shown. A time-gate may be disposed between a gate initiating time 118 and a gate-closing time 120. The initiating and closing times may be predetermined according to a calibrating procedure. In FIG. 3, the time-gated portion 116 of the echo profile is free of significant return pulses because such flaws are not present in the structure 100 in FIG. 2. More particularly, such flaws are not present in the structure under the ultrasonic transducer device 302.

Figure 4:
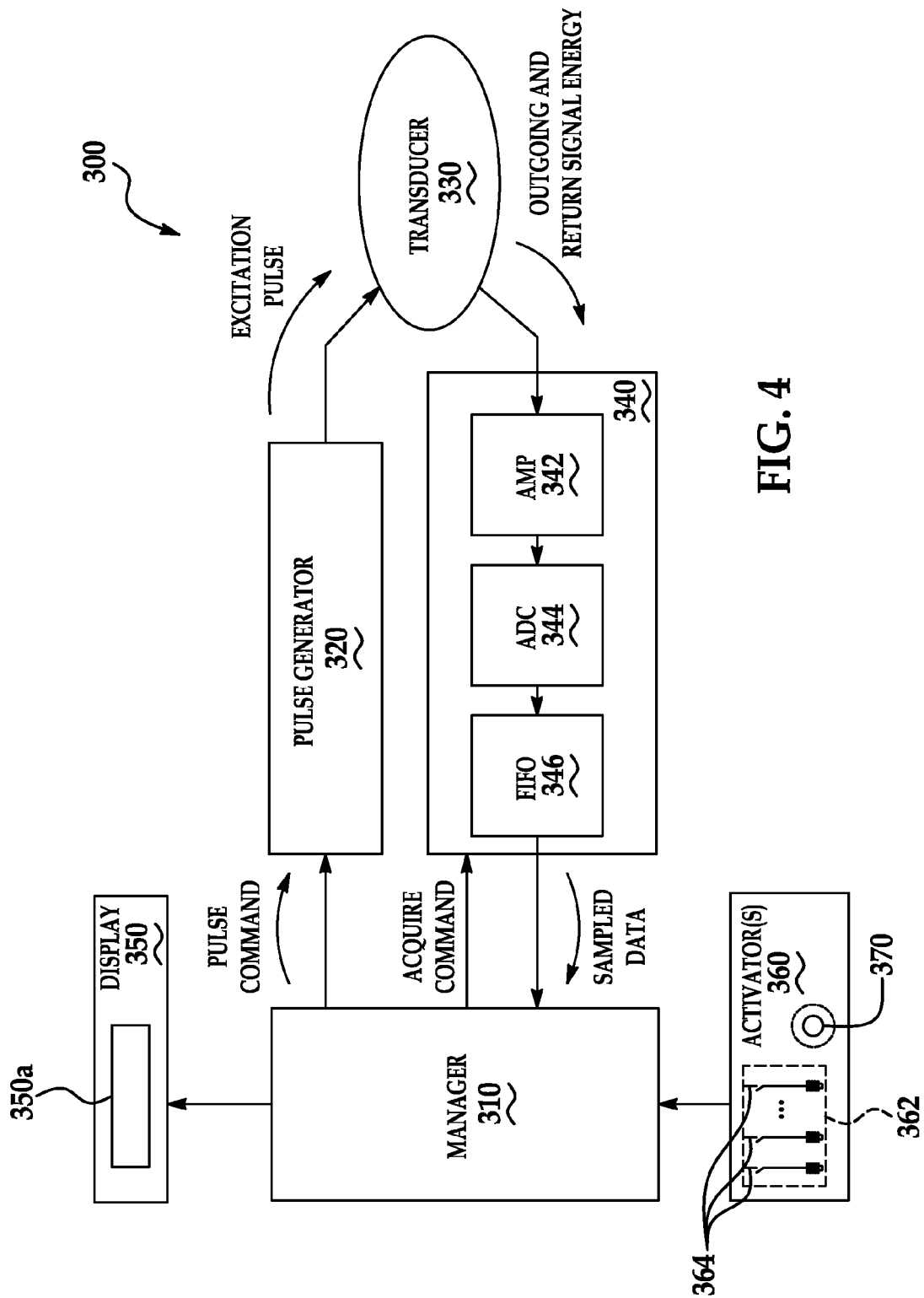
FIG. 4 is a block diagram representing exemplary embodiments of electronic circuits of the diagnostic apparatus of FIG. 1.

FIG. 4 is a block diagram representing exemplary embodiments of electronic circuits and connections of the diagnostic apparatus 300. As shown in FIG. 4, the diagnostic apparatus 300 may include a manager 310, a pulse generator 320, the transducer 330, a data acquisition device 340, the display 350 represented to include a porosity indicator 350a, and a number of activators 360 represented to include at least the multiple switches 364 of the activator assembly 362 and a calibration activator 370. FIG. 4 represents the circuits and connections without particular regard to physical arrangements of circuit components. Thus, while other arrangements may be well within the scope of these descriptions of FIG. 4, the ultrasonic transducer device 302 of FIG. 1, to which the activator assembly 362 is attached, may include the transducer 330, while the electronic device 304 of FIG. 1 may include the display 350, the calibration activator 370, the manager 310, the pulse generator 320 and the data acquisition device 340. The data acquisition device 340 may include an amplifier (AMP) 342, an analog to digital converter (ADC) 344 and a first-end-first-out buffer (FIFO) 346. While the diagnostic apparatus 300 is represented to include a collection of various integrated circuits and other components coupled together on a single circuit-board, it should be appreciated that the diagnostic apparatus 300 can take other forms. For example, in various embodiments, the pulse generator 320, as well as the FIFO 346 and ADC 344, may be incorporated into a bussed structure such as that commonly used on many processor-based systems. In still other embodiments, it should be appreciated that many of the illustrated components may be incorporated on a single integrated circuit, with the understanding that the display, transducer, and activators might be located off-chip.

For the exemplary electronic circuits and connections of FIG. 4, there may be at least two modes of operation: a calibration mode for executing calibration cycles to calibrate the diagnostic apparatus 300; and a test mode for executing test cycles to use the apparatus to measure the porosity of a structure. Execution of the calibration mode of the diagnostic apparatus 300 may entail calibrating the apparatus against a calibration structure in a relatively simple, time-efficient, and cost-effective procedure. In comparison, calibration procedures for other types of inspection devices can require that technicians spend hours characterizing the various components within the devices. It is expected that the diagnostic apparatus 300 may be calibrated by trained NDI specialists, who may be stationed at particular NDI and equipment calibration facilities. The calibrated diagnostic apparatus may then be distributed for use, for example, by maintenance crews at aviation facilities.

To start a calibration cycle, an operator may initially press the transducer device 302 against a calibration structure, causing simultaneous actuations of all of the switches 364 (FIG. 1) of the activator assembly 362. The operator may additionally actuate the calibration activator 370, which can be, for example, a hidden or locked switch. For example, the calibration activator 370 may be disposed within the housing 308 of the electronic device 304 (FIG. 1) and hidden from typical maintenance crew operators so that only NDI specialists typically actuate the calibration activator. Alternatively, the calibration activator 370 may be recessed but available along the exterior of the housing for actuation by a stylus in order to prevent inadvertent actuation, which could cause a loss of established calibration. Actuations of the switches 364 may permit activation of the ultrasonic transducer 330, and actuation of the calibration activator 370 may provide the manager 310 with an indication that a calibration cycle is desired. In response to these actuations, the manager 310 may generate a command signal to the pulse generator 320. The pulse generator 320 may, in turn, receive the command signal from manager 310 and send an excitation pulse having a particular amplitude and duration to the transducer 330. The transducer 330 may receive the excitation pulse and emit a burst of ultrasonic energy, referred to herein as an outgoing pulse or main bang.

In the exemplary diagnostic apparatus 300 of FIG. 4, the pulse generator 320 can accept a TTL-compatible command signal, such as a low-to-high transition, and generate an excitation pulse having an amplitude of about 25-30 volts and a duration of about 200 nanoseconds. However, it should be appreciated that other types of command signals and excitation pulses are within the scope of these descriptions. The transducer 330 may generally both send outgoing pulses and detect echo profiles returning to the transducer 330. The transducer 330 may transform echo profiles of ultrasonic energy into electrical analog signals that are received by the data acquisition device 340. Signals received by the data acquisition device 340 may be passed to the amplifier 342 which can buffer, amplify and filter the electric analog signals which then pass to the ADC 344. The ADC 344 may convert analog electrical signals to digital data. Subsequently, the digital data may be passed to FIFO 346, where it can be stored until extracted by the manager 310.

Figure 5:
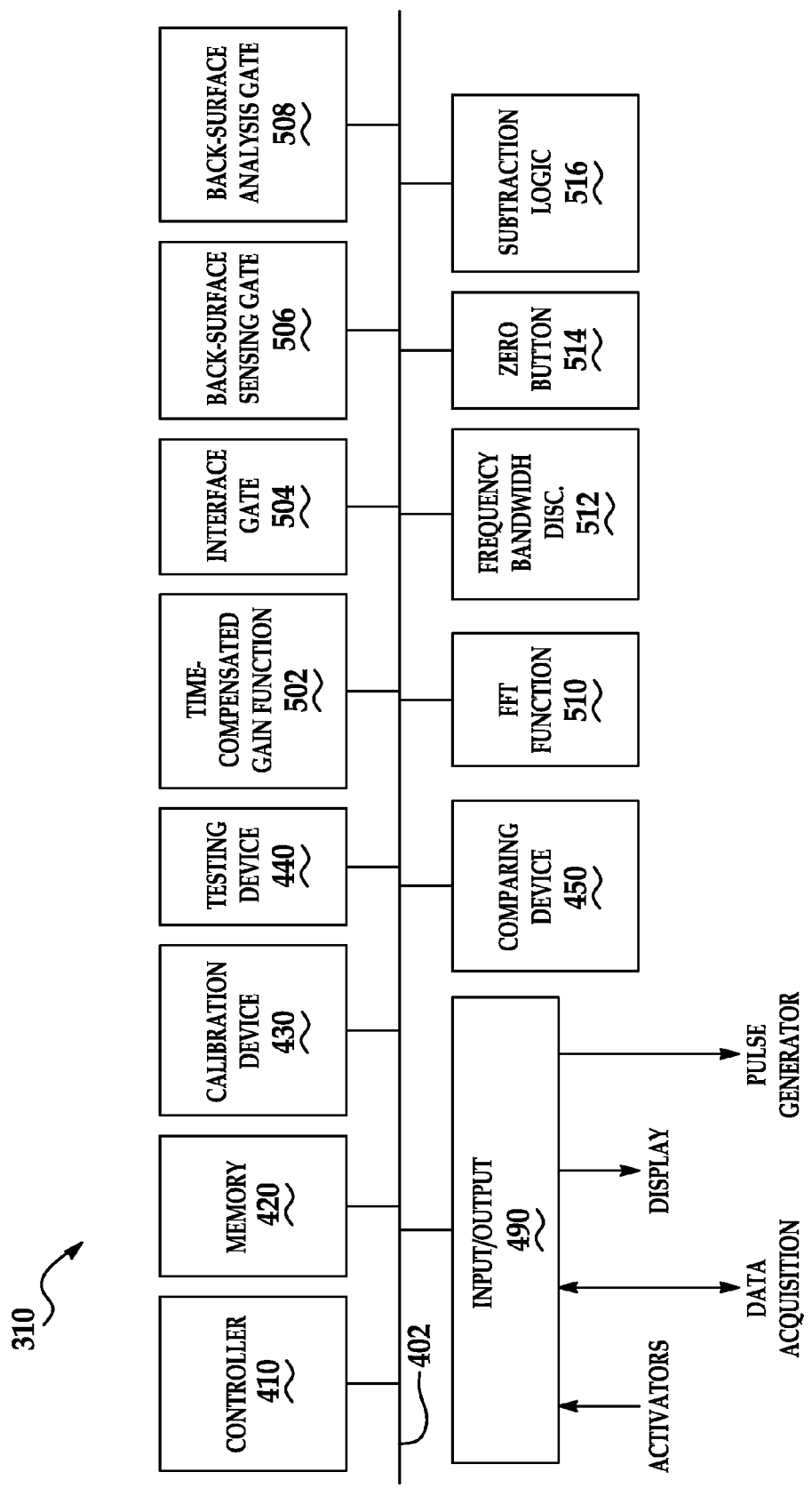
FIG. 5 is a block diagram representing an exemplary embodiment of the manager of FIG. 4.

FIG. 5 is a block diagram of an exemplary embodiment of the manager 310 of FIG. 4. As shown in FIG. 5, the manager 310 may include a controller 410, a memory 420, a calibration device 430, a testing device 440, a comparing device 450 and an input/output port 490. The manager 310 may further include a time-compensated gain function 502, an interface gate 504, a back-surface sensing gate 506, a back-surface analysis gate 508, an FFT (Fast Fourier Transform) function 510, a frequency bandwidth discriminator 512, a zero button 514 and a subtraction logic 516. In some embodiments, the various components of the manager 310 may be coupled together by way of a data/address bus 402. While the exemplary manager 310 is depicted as a device having a bussed architecture with various peripherals, it should be appreciated that in other embodiments, the manager 310 can appear as a single-chip processor with integrated components, a general purpose processor, a digital signal processor, a programmable logic chip (PLC) executing software, or any other system capable of executing a series of instructions from a memory. Furthermore, it should be appreciated that the manager 310 can take the form of any number of discrete logic circuits capable of performing the various required functions as described herein. Still further, it should be appreciated that, in various other embodiments, components of the manager 310, such as the calibration device 430, the testing device 440 and the comparing device 450, can take the form of various programs and routines embedded in the memory 420.

The interface gate 504 may be adapted to identify and lock onto the back surface echo of the structure 100 the porosity of which is being detected. The back surface sensing gate 506 may be adapted to cover the interval from the beyond the front surface to an end point far out in time ending just short of the delay line multiple and sense the peak signal in this interval. The back surface analysis gate 508 may be adapted to center on the back-surface signal which is found by the back surface sensing gate 506 and define the limits of the FFT signal capture. The FFT function 510 may be adapted to perform an FFT of the back surface signal which is captured by the back surface analysis gate 508. The frequency bandwidth discriminator 512 may be adapted to isolate a frequency bandwidth of selected frequency (such as 0.9 MHz to 1.1 MHz, for example and without limitation) in the back-surface echo signal and may be adapted to measure the amplitude of only that part of the FFT spectrum. The zero button 514 may be adapted to memorize the amplitude of the part of the FFT spectrum which is isolated and measured by the frequency bandwidth discriminator 512. In practice, this may be a baseline point such as a reading taken on pristine CFRP step wedges used by airlines. The porosity indicator 350a of the display 350 may be adapted to display a porosity reading of "0 percent" when the reference amplitude is memorized by depression of the zero button 514. The subtraction logic 516 may be adapted to compare subsequent amplitude variations to the stored "zero" reference amplitude reading and display the equivalent porosity level directly using a stored 1 MHz attenuation slope or look-up table linked to the structure 100 which is being examined.

After data acquisition has started, the manager 310 may extract information from the FIFO 346 (FIG. 4) and store the information in a local memory 420 for use in a test cycle. In particular, the manager 310 may be configured to determine at least the TOF of back-surface return pulses detected during calibration cycles. The manager 310 may identify the pulse having the greatest amplitude following the expected TOF of a front-surface return pulse. Insofar as the ultrasonic transducer device 302 is pressed against the surface of a good structure when a calibration cycle is initiated, only back-surface return pulses may follow front-surface return pulses and exceed the established threshold 122 as shown in FIG. 3. The threshold may be established as a parameter within software executed by the manager. A test point may be available within the housing, for example upstream or downstream of the amplifier 342, so that a calibration specialist can sample and view echo profiles such as that shown in FIG. 3 to confirm the programming of the manager and the performance of the diagnostic apparatus 300. The manager may automatically set the gate-closing time 120 (FIG. 3) 10 to precede the TOF of the identified back-surface return pulse. For example, the manager may subtract a fixed or adjustable time decrement from the TOF of back surface return pulses to establish the gate-closing time.

The expected TOF of a front-surface return pulse may be a permanent parameter, an adjustable parameter, or may be automatically determined by the manager 310. The expected TOF of a front-surface return pulse may correspond approximately to the time elapsed as an ultrasonic pulse twice traverses the length of the coupling element as measured between the proximal and distal ends 334 and 336 thereof. Thus, in embodiments of the ultrasonic transducer device 302 wherein the coupling element 332 is a fixed component, the TOF of an ultrasonic pulse that 20 travels from the proximal end to the distal end, and back again, may be a fixed time interval and thus may be a permanent parameter. Alternatively, a front-surface return pulse may be identified by the manager 310 as the earliest return pulse that exceeds a threshold. Thus, the TOF of a front-surface return pulse may be automatically determined. Whether the expected TOF of a front-surface return pulse is a permanent parameter or is automatically determined, an adjustment device may be hidden within the housing 308 of the electronic device 304 so that a calibration specialist can make adjustments affecting the parameter or determination. The gate-initiating time 118 (FIG. 3) typically closely follows the expected TOF of a front-surface return pulse so that the diagnostic apparatus is calibrated to be sensitive to shallow flaws such as delaminations disposed in a measured structure near the front surface. The manager may automatically set the gate-initiating time 118 (FIG. 3) to follow the TOF of front-surface return pulses. For example, the manager may add a fixed or adjustable time increment to the TOF of front-surface return pulses to establish the gate-initiating time. For example, such a time increment may be established as a parameter within software executed by the manager 310. The manager 310 generally coordinates a calibration cycle once the calibration activator is actuated, and the ultrasonic transducer device is pressed against a surface. In response, the manager 310 may issue a command signal to the pulse generator 320 shown in FIG. 4, as well as a capture signal to the data acquisition device 340. The controller 410 may subsequently import captured calibration-cycle data by way of the input/output port 490, and store the captured data in the memory 420. The controller 410 may then move the captured calibration-cycle data from the memory 420 to the calibration device 430. As the calibration device 430 receives the calibration-cycle data, it may perform operations to identify return pulses and to determine the amplitudes and times-of-flight of return pulses. Furthermore, the calibration device may characterize pulse shape information, and phase information. During calibration cycles, the calibration device 430 typically at least detects back-surface return echoes which may exhibit distortions and noise contaminations that can be abated or compensated by the calibration device. Return echoes may be corrupted by excessive noise and return-echoes may be caused by unexpected defects. The calibration device 430 may be configured to recognize that received data is problematic and subsequently issue an indication that a problem with the calibration cycle has occurred. Assuming that a calibration specialist receives such an indication, the specialist can perform a second calibration cycle on another portion of the subject laminate structure until a good calibration cycle is performed and valid calibration is established. Furthermore, the manager 310 may coordinate a single calibration cycle wherein a single outgoing pulse is sent and a corresponding echo profile is detected, or the manager 310 may coordinate a plurality of calibration cycles and utilize statistical processing to determine calibration parameters such as gate-initiating and gate-closing times.

Once calibration of the diagnostic apparatus is established, the apparatus can be distributed to an operator such as a member of a maintenance crew at an aviation facility. An operator can then press the ultrasonic transducer device 302 against a surface of a structure in order to quantify the porosity level of attenuative areas identified within the structure 100 between the depths respectively corresponding to the established gate initiating and closing times. Assuming the power switch 356 (FIG. 2) is closed, simultaneous actuations of all of the multiple switches 364 may cause the initiation of a test cycle. As with the calibration mode, the manager 310 may send a command signal to the pulse generator 320, which may in turn send an excitation pulse to the transducer 330. The transducer 330 may emit an outgoing ultrasonic pulse, detect return echoes, and generate an electrical signal which conveys echo profile information to the data acquisition device 340. The controller 410 may subsequently import captured test-cycle data by way of the input/output port 490, and store the captured data in the memory 420. The controller 410 may then move the captured test-cycle data from the memory 420 to the testing device 440. As the testing device 440 receives the test-cycle data, it may perform operations to identify return echoes and to determine the amplitudes and times-of-flight of return echoes. The comparing device 450 may receive return-echo amplitude and TOF data from the testing device and determine whether any return echoes exceeding the established threshold are present within the established time gate defined between the gate-initiating and gate-closing times 118 and 120 (FIG. 3). The manager 310 may coordinate a single test cycle wherein a single outgoing pulse is sent and a corresponding echo profile is detected, or the manager 310 may coordinate a plurality of test cycles and utilize statistical processing to determine whether any return pulses exceeding the established threshold are present within the established time gate. With further regard to the calibration of the diagnostic apparatus 300, a calibration cycle can be initiated with the ultrasonic transducer device 302 pressed against a good portion of a structure, as shown in FIG. 2, in order to prepare for testing other portions of the structure. However, the assurance of the calibration of the diagnostic apparatus following such a calibration procedure may be as questionable as any assumption that a good portion of a structure was interrogated. Thus, a calibration structure can be provided in order to assure that calibration is completed on a well characterized material sample. When checking the porosity level of indications found in a bonded repair, the procedure may include calibration on material outside the repair (assumed to be zero percent porosity) and then compare the amplitude of the indication from inside the repair. The change in amplitude is an indication of the porosity level associated with the repair indication.

The interface gate 504 identifies and locks onto the back surface echo of the structure 100 the porosity of which is being detected. The back surface sensing gate 506 captures the interval from beyond the front surface to an end point far out in time and ends just short of the delay line multiple and senses the peak signal in this interval. The back surface analysis gate 508 centers on the back-surface signal which is found by the back surface sensing gate 506 and defines the limits of the FFT signal capture. The FFT function 510 performs an FFT of the back surface signal which is captured by the back surface analysis gate 508. The frequency bandwidth discriminator 512 isolates a frequency bandwidth of selected frequency (such as 0.9 MHz to 1.1 MHz, for example and without limitation) in the back-surface echo signal and measures the amplitude of only that part of the FFT spectrum. The zero button 514 memorizes the amplitude of the part of the FFT spectrum which is isolated and measured by the frequency bandwidth discriminator 512. In practice, this may be a baseline point such as a reading taken on pristine CFRP step wedges used by airlines. The porosity indicator 350a of the display 350 displays a porosity reading of "0 percent" when the reference amplitude is memorized by depression of the zero button 514. The subtraction logic 516 compares subsequent amplitude variations to the stored "zero" reference amplitude reading and displays the equivalent porosity level directly using a stored 1 MHz attenuation slope or look-up table linked to the structure 100 which is being examined.

In alternative embodiments, the porosity detection algorithm may include features that compare the FFT signals between areas of nominal and elevated porosity and quantify spectral difference between the two FFT envelopes. This may involve measurement of the frequency bandwidth change (the distance between the −6 dB points, for example), the center frequency shift, or the asymmetry of the envelope caused by elevated porosity levels.

Figure 6A:
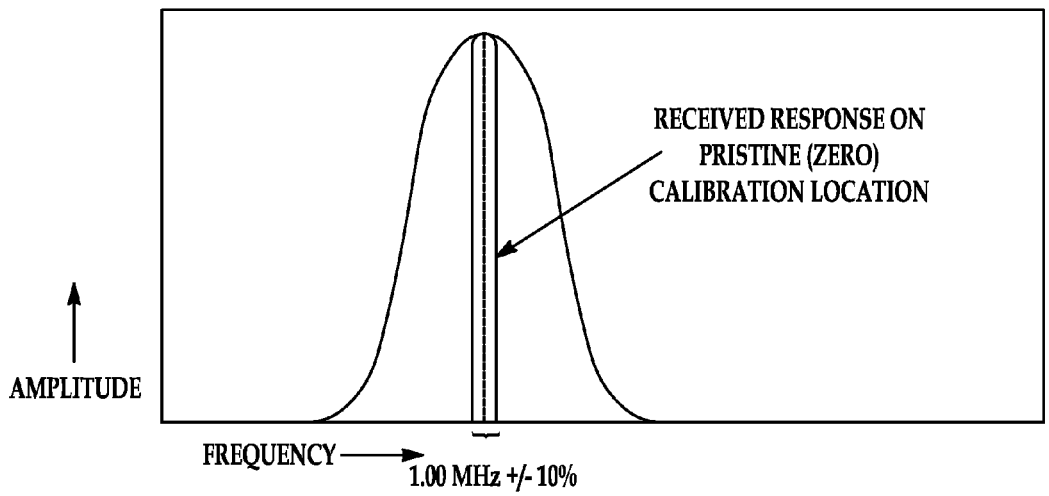
FIG. 6A is an amplitude vs. frequency curve which illustrates the difference between a zero reading location and a pristine calibration location.
Figure 6B:
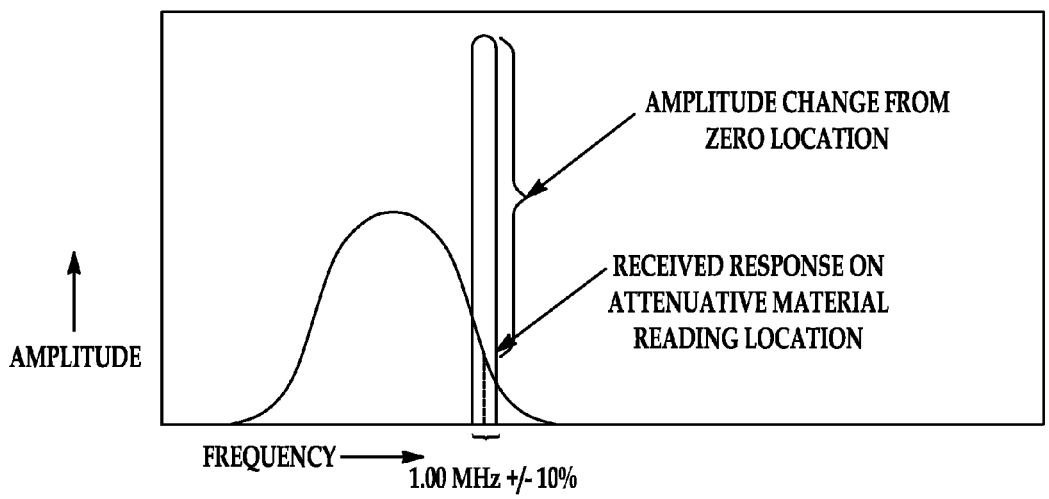
FIG. 6B is an amplitude vs. frequency curve which illustrates the amplitude change from a zero reading location to a received response on an attenuative material reading location.

An example of the attenuation difference between a zero reading location and a subsequent measurement location on attenuative material is shown in FIGS. 6A and 6B. The measured amplitude change may be compared to a stored look-up table or attenuation slope and scaled to display an actual percent porosity on an LCD readout. The look-up table may be stored a priory or developed on the spot by recording readings from different known porosity standards or analogues. In the latter case, after nulling the instrument on a pristine specimen, the displayed response from a known-porosity calibration standard may be adjusted until it matches the value displayed on the standard. Once the values match, the resulting attenuation slope may be entered into the electronics as part of the pre-inspection calibration. This may be similar to the routine used for ultrasonic thickness testing devices.

It will be appreciated by those skilled in the art that the porosity measurement apparatus and method simplify porosity measurements and render such measurements more accurate. The device and method may allow airline users to make measurements on bonded repairs for exact porosity levels after a pulse-echo A-scan or C-scan method flags areas as being suspect. The device and method may eliminate the need for look-up tables and may display the porosity result directly and with greater accuracy. The device and method may be calibrated for various materials to extend its use to other composite laminate applications such as materials in the marine industry or the wind power industry, for example and without limitation.

Figure 7:
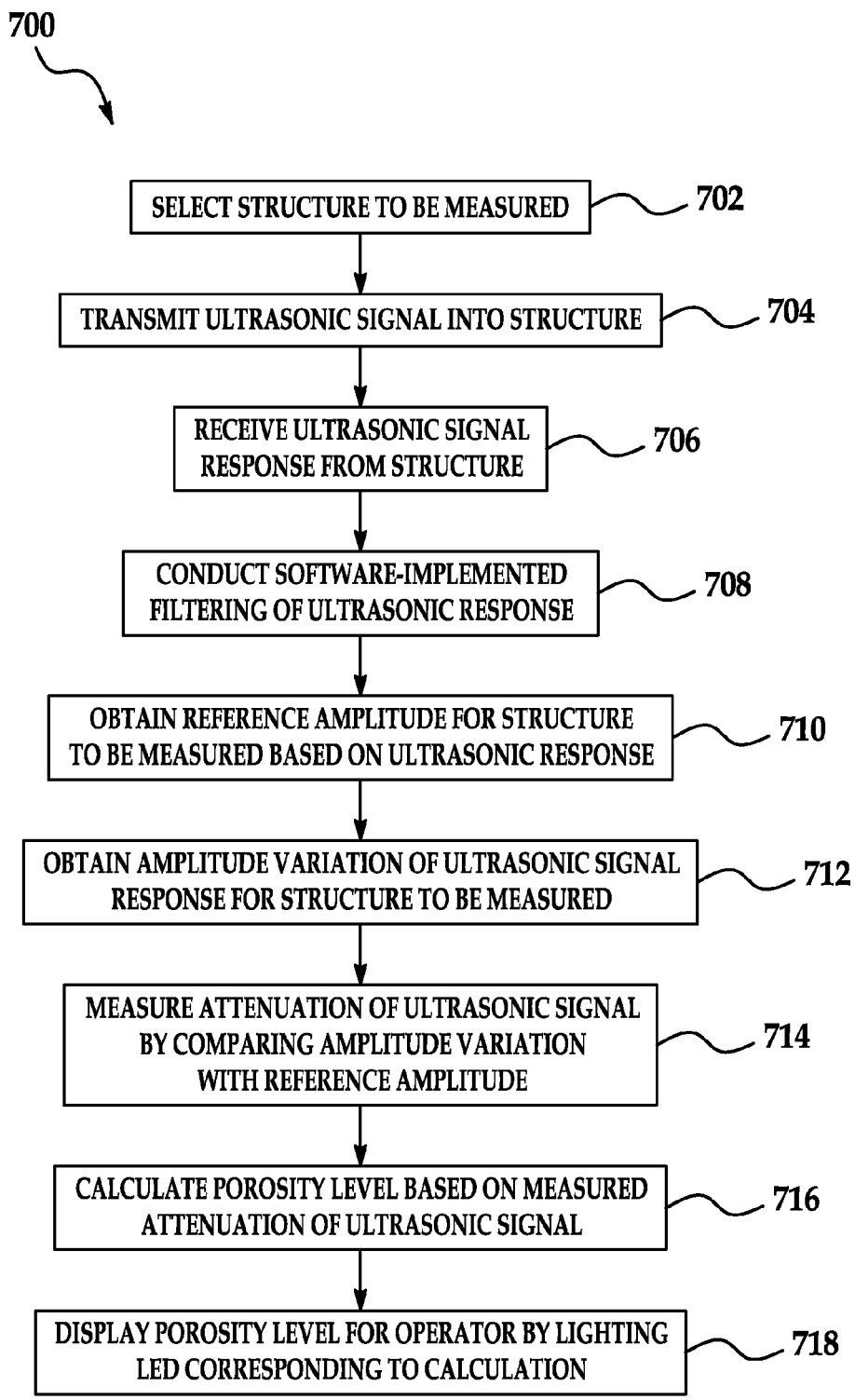
FIG. 7 is a flow diagram of an illustrative embodiment of a direct-reading porosity measurement method.
Figure 8:
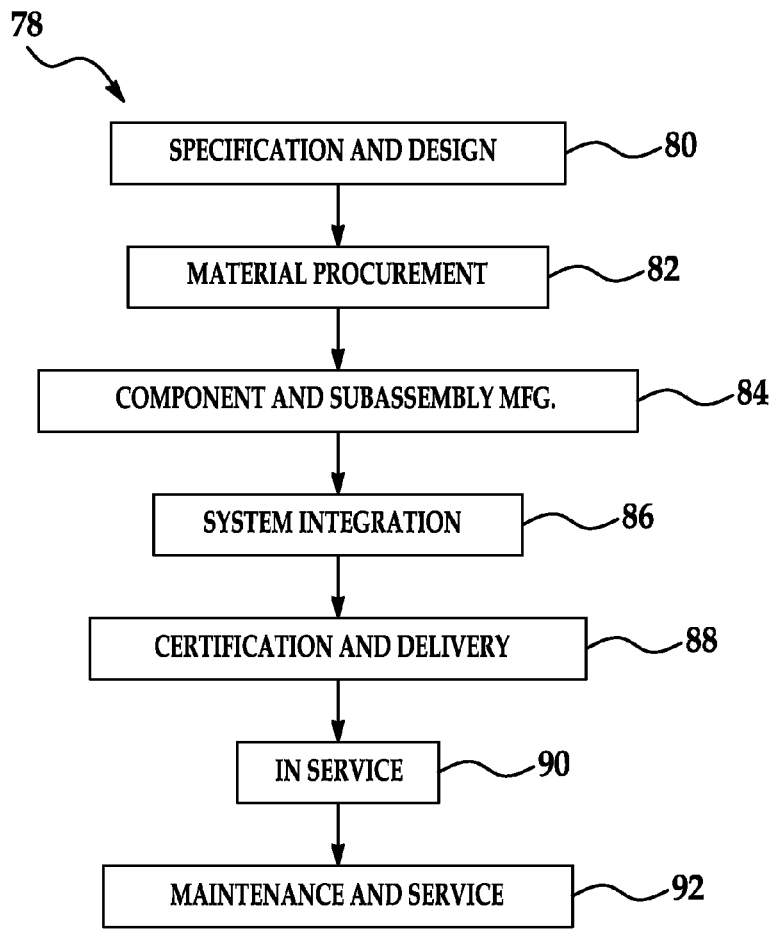
FIG. 8 is a flow diagram of an aircraft production and service methodology.
Figure 9:
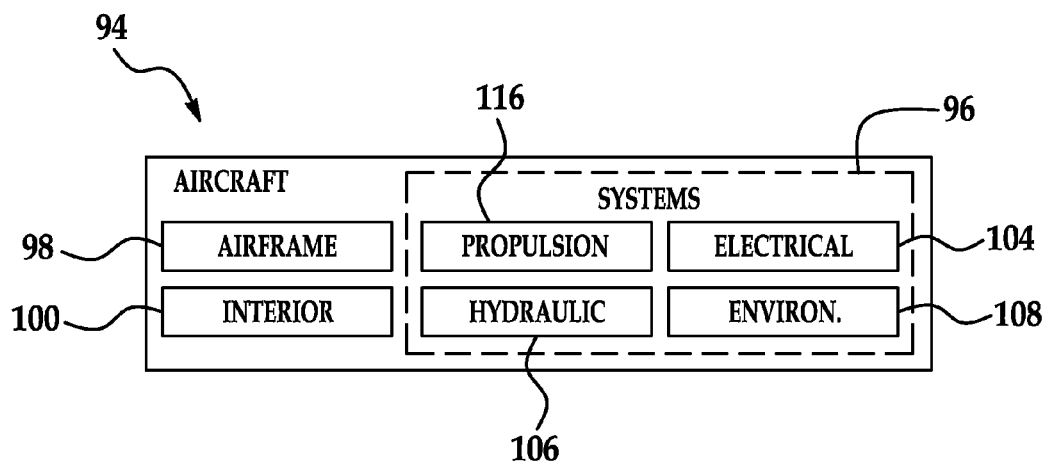
FIG. 9 is a block diagram of an aircraft.

Referring to FIG. 7, a flow diagram 700 of an illustrative embodiment of a direct-reading porosity measurement method is shown. In block 702, a polymeric composite structure the porosity of which is to be measured may be selected. In block 704, an ultrasonic signal may be transmitted into the structure. In block 706, an ultrasonic signal response may be received from the structure. In block 708, software-implemented filtering of the ultrasonic response may be conducted. In block 710, a reference amplitude for the structure to be measured based on the ultrasonic response may be obtained. In block 712, at least one amplitude variation of the ultrasonic signal response for the structure to be measured may be obtained. In block 714, the attenuation of the ultrasonic signal may be measured by comparing the amplitude variation or variations with the reference amplitude. In block 716, the porosity level of the structure may be calculated based on the measured attenuation of the ultrasonic signal. In block 718, the porosity level may be displayed for the operator by lighting an LED corresponding to the calculation. In some embodiments, the porosity level may be displayed as a percentage.

Though several advantages of embodiments of the present disclosure are described herein, it should be understood that other advantages and other embodiments of the present disclosure are within the scope of these descriptions. Indeed, many modifications and other embodiments of the disclosure set forth herein may come to mind to one skilled in the art to which the disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for measuring porosity of a structure, comprising:
    an ultrasonic transducer device configured to be pressed against a structure, the structure having a front surface and a back surface, the ultrasonic transducer device being further configured to emit ultrasonic pulses into the structure through the front surface and detect echo profiles; and
    an electronic device including:
        a manager having an interface gate adapted to cover a front surface ultrasonic pulse entering the front surface of the structure, a back-surface sensing gate adapted to cover an interval from beyond the front surface of the structure to an end point far out in time, a back surface analysis gate adapted to center over the back surface of the structure and define limits of a signal capture, and a frequency-bandwidth discriminator adapted to isolate a frequency bandwidth in a back surface echo signal captured by the back surface analysis gate and measure a reference amplitude of the frequency bandwidth;
        a pulse generator interfacing with the manager and the ultrasonic transducer device;
        a data acquisition device interfacing with the ultrasonic transducer device and the manager; and
        a display having a porosity indicator interfacing with the manager.

2. The apparatus of claim 1 wherein the porosity indicator is adapted to indicate porosity as a percentage.

3. The apparatus of claim 1 wherein the manager comprises a time-compensated gain function.

4. The apparatus of claim 1 wherein the manager further comprises a zero button adapted to memorize the reference amplitude of the frequency bandwidth upon depression of the zero button.

5. The apparatus of claim 4 wherein the porosity indicator of the display is adapted to display a zero percent reading when the reference amplitude is memorized by depression of the zero button.

6. The apparatus of claim 5 wherein the manager further comprises a subtraction logic adapted to compare subsequent amplitude variations to the zero percent reading and display an equivalent porosity level directly on the porosity indicator using a stored 1 MHz attenuation slope or a look-up table linked to the structure.

7. The apparatus of claim 1 wherein the frequency-bandwidth discriminator is adapted to isolate a frequency bandwidth of from about 0.9 MHz to about 1.1 MHz in the back-surface echo signal.

8. An apparatus for measuring porosity of a structure, comprising:
   an ultrasonic transducer device configured to be pressed against a structure, the structure having a front surface and a back surface, the ultrasonic transducer device being further configured to emit ultrasonic pulses into the structure through the front surface and detect echo profiles; and
   an electronic device including:
      a manager having an interface gate adapted to cover a front surface ultrasonic pulse entering the front surface of the structure, a back-surface sensing gate adapted to cover an interval from beyond the front surface of the structure to an end point far out in time, a back surface analysis gate adapted to center over the back surface of the structure and define limits of a fast fourier transformation signal capture, a fast fourier transformation function adapted to perform a fast fourier transformation of the back surface signal captured by the back surface analysis gate, and a frequency-bandwidth discriminator adapted to isolate a frequency bandwidth in a back surface echo signal captured by the back surface analysis gate and measuring a reference amplitude of the frequency bandwidth;
      a pulse generator interfacing with the manager and the ultrasonic transducer device;
      a data acquisition device interfacing with the ultrasonic transducer device and the manager; and
      a display having a porosity indicator interfacing with the manager.

9. The apparatus of claim 8 wherein the porosity indicator is adapted to indicate porosity as a percentage.

10. The apparatus of claim 8 wherein the manager comprises a time-compensated gain function.

11. The apparatus of claim 8 wherein the manager further comprises a zero button adapted to memorize the reference amplitude of the frequency bandwidth upon depression of the zero button.

12. The apparatus of claim 11 wherein the porosity indicator of the display is adapted to display a zero percent reading when the reference amplitude is memorized by depression of the zero button.

13. The apparatus of claim 12 wherein the manager further comprises a subtraction logic adapted to compare subsequent amplitude variations to the zero percent reading and display an equivalent porosity level directly on the porosity indicator using a stored 1 MHz attenuation slope or a look-up table linked to the structure.

14. The apparatus of claim 8 wherein the frequency-bandwidth discriminator is adapted to isolate a frequency bandwidth of from about 0.9 MHz to about 1.1 MHz in the back-surface echo signal.

15. A porosity measurement method, comprising:
   selecting a structure to be measured;
   transmitting an ultrasonic signal into the structure;
   receiving an ultrasonic signal response from the structure;
   filtering the ultrasonic response;
   obtaining a reference amplitude for the structure to be measured based on the ultrasonic response;
   obtaining at least one amplitude variation of the ultrasonic signal response for the structure to be measured;
   measuring attenuation of the ultrasonic signal by comparing the amplitude variation of the structure to be measured with the reference amplitude; and
   calculating a porosity level of the structure based on the measured attenuation of the ultrasonic signal.

16. The method of claim 15 wherein selecting a structure to be measured comprises selecting a polymeric composite structure.

17. The method of claim 15 further comprising displaying the porosity level of the structure.

18. The method of claim 15 wherein calculating a porosity level of the structure comprises calculating a percentage porosity of the structure.

19. An apparatus, comprising:
   an ultrasonic transducer configured to transmit an ultrasonic signal into a structure and to receive an ultrasonic signal response from the structure; and
   a manager configured to identify an amplitude variation of the ultrasonic signal response, to determine attenuation of the ultrasonic signal by comparing the amplitude variation to a reference amplitude, and to calculate a porosity level of the structure based on the attenuation of the ultrasonic signal.

20. The apparatus of claim 19 further comprising a display configured to display an indication of the porosity level of the structure as a percentage porosity of the structure.

* * * * *